US011035866B2

(12) United States Patent
Pollard et al.

(10) Patent No.: US 11,035,866 B2
(45) Date of Patent: *Jun. 15, 2021

(54) BIOMARKERS FOR SEIZURES

(71) Applicant: The Trustees of the University of Pennsylvania, Philadelphia, PA (US)

(72) Inventors: John Robert Pollard, Wallingford, PA (US); Peter B. Crino, Moorestown, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,385

(22) Filed: May 11, 2018

(65) Prior Publication Data

US 2018/0259540 A1 Sep. 13, 2018

Related U.S. Application Data

(63) Continuation of application No. 15/678,784, filed on Aug. 16, 2017, now Pat. No. 9,983,219, which is a continuation of application No. 15/061,329, filed on Mar. 4, 2016, now Pat. No. 9,772,335, which is a continuation of application No. 14/943,101, filed on Nov. 17, 2015, now abandoned, which is a continuation of application No. 14/001,306, filed as application No. PCT/US2012/026467 on Feb. 24, 2012, now abandoned.

(60) Provisional application No. 61/446,461, filed on Feb. 24, 2011.

(51) Int. Cl.
| | |
|---|---|
| *G01N 33/68* | (2006.01) |
| *G01N 33/543* | (2006.01) |
| *A61K 38/17* | (2006.01) |

(52) U.S. Cl.
CPC ..... *G01N 33/6896* (2013.01); *A61K 38/1709* (2013.01); *G01N 33/543* (2013.01); *G01N 2333/521* (2013.01); *G01N 2333/705* (2013.01); *G01N 2333/70503* (2013.01); *G01N 2333/70525* (2013.01); *G01N 2800/2857* (2013.01)

(58) Field of Classification Search
CPC ..... A61P 25/00; A61P 25/08; G01N 33/6896; G01N 33/543; G01N 2333/70503; G01N 2333/70525; G01N 2333/521; G01N 2333/705; G01N 2800/2857; A61K 38/1709

See application file for complete search history.

(56) References Cited

U.S. PATENT DOCUMENTS

| | | | |
|---|---|---|---|
| 7,585,968 B2 | 9/2009 | Karras et al. | |
| 8,293,489 B2 | 10/2012 | Henkin | |
| 8,663,938 B2 | 3/2014 | Henkin | |
| 2006/0234972 A1 | 10/2006 | Karras et al. | |
| 2008/0188461 A1 | 8/2008 | Guan et al. | |
| 2009/0099031 A1 | 4/2009 | Stemmer et al. | |
| 2010/0124756 A1 | 5/2010 | Ray et al. | |
| 2011/0305663 A1 | 12/2011 | Gosselin et al. | |
| 2012/0058484 A1 | 3/2012 | Heit | |

FOREIGN PATENT DOCUMENTS

| | | |
|---|---|---|
| JP | 07242697 | 9/1995 |
| WO | WO 2006/047417 A2 | 5/2006 |
| WO | WO 2010/059242 A2 | 5/2010 |

OTHER PUBLICATIONS

Borusiak, et al., Soluble Telencephalin in the Serum of Children after Febrile Seizures, J. Neurol., 2005, Epub Feb. 23, 2005, 252:493-494.
Choi, et al., Cellular Injury and Neuroinflammation in Children with Chronic Intractable Epilepsy, Journal of Neuroinflammation, Dec. 19, 2009, 6:38 (14 pages).
Echigo, et al., Both Th1 and Th2 chemokines are elevated in sera of patients with autoimmune blistering diseases, Arch Dermatol Res. Jun. 2006;298(1):38-45. Epub Apr. 1, 2006.
Fujii, et al., Serum levels of a Th1 chemoattractant IP-10 and Th2 chemoattractants, TARC and MDC, are elevated in patients with systemic sclerosis, J Dermatol Sci. Jun. 2004;35(1):43-51.
Jansen, et al., Cognitive fMRI and Soluble Telencephalin Assessment in Patients with Localization-Related Epilepsy, Acta Neurol Scand, Oct. 2008, 118:232-239.
Lamparello, et al., Developmental lineage of cell types in cortical dysplasia with balloon cells, Brain, Sep. 2007, 130(9):2267-2276.
Lehtimaki, et al., Increased Plasma Levels of Cytokines after Seizures in Localization-Related Epilepsy, Acta Neurol Scand, Oct. 2007, 116(4):226-230.
Leung, et al., Plasma TARC concentration may be a useful marker for asthmatic exacerbation in children, Eur Respir J. Apr. 2003;21(4):616-20.
Lindsberg, et al., Release of Soluble ICAM-5, a Neuronal Adhesion Molecule, in Acute Encephalitis, Neurology, Feb. 12, 2002; 58(3):446-451.
Maguire, et al., Epilepsy (generalized), BMJ Clin Evid., Jun. 2010, 06:1201, pp. 1-14.
Mizuno, et al., Neuronal Adhesion Molecule Telencephalin Induces Rapid Cell Spreading of Microglia, Brain Research, Dec. 1999, 849:58-66.
Nakazato, et al., Serum levels of Th2 chemokines, CCL17, CCL22, and CCL27, were the important markers of severity in infantile atopic dermatitis, Pediatr. Allergy Immunol., Nov. 2008;19(7):605-13.

(Continued)

*Primary Examiner* — Kimberly Ballard
*Assistant Examiner* — Stacey N MacFarlane
(74) *Attorney, Agent, or Firm* — Howson & Howson LLP; Colleen M. Schaller

(57) ABSTRACT

The application relates to markers for seizures and epilepsy. Polypeptide expression panels or arrays are provided, comprising one or more probes capable of binding specific polypeptides in blood plasma or blood serum of a mammalian subject. Also provided are methods for detecting seizure, methods for predicting seizure, use of sICAM-5 in the treatment of seizure, methods for assessing the effectiveness of a treatment of seizure, and diagnostic kits.

6 Claims, 13 Drawing Sheets

(56) References Cited

OTHER PUBLICATIONS

Niens, et al., Serum chemokine levels in Hodgkin lymphoma patients: highly increased levels of CCL17 and CCL22, Br J Haematol. Mar. 2008;140(5):527-36.

Palmio, et al., Elevated Serum Neuron-Specific Enolase in Patients with Temporal Lobe Epilepsy, Epilepsy Research, Oct. 2008, available online on Jul. 1, 2008, 81(2-3):155-160.

Pardo, et al., Immunity, Neuroglia and Neuroinflammation in Autism, International Review of Psychiatry, Dec. 2005, 17(6):485-496.

Pollard, et al., The TARC/sICAM5 ratio in patient plasma is a candidate biomarker for drug resistant epilepsy, Frontiers in Neurology: Epilepsy, Jan. 3, 2013, 3(181):1-8, e-pub 2012.

Rieckmann, et al., Telencephalin as an Indicator for Temporal-Lobe Dysfunction, Lancet, Aug. 1, 1998, 352(9125):370-371.

Shimada, et al., Both Th2 and Th1 chemokines (TARC/CCL17, MDC/CCL22, and Mig/CXCL9) are elevated in sera from patients with atopic dermatitis, J Dermatol Sci. May 2004;34(3):201-8.

Sinha, et al., Do Cytokines Have Any Role in Epilepsy?, Epilepsy Research, available online Sep. 9, 2008, 82:171-179.

Spradling, et al., Transcriptional Responses of the Nerve Agent-Sensitive Brain Regions Amygdala, Hippocampus, Piriform Cortex, Septum, and Thalamus Following Exposure to the Organophosphonate Anticholinesterase Sarin, J. Neuroinflammation, Jul. 21, 2011, 8:84 (21 pages).

Tian, et al., Shedded Neuronal ICAM-5 Suppresses T-cell Activation, Blood, prepublished online Jan. 25, 2008, Apr. 1, 2008, 111(7):3615-3625.

Vezzani, et al., The Role of Inflammation in Epilepsy, Nature Reviews: Neurology, prepublished online Dec. 7, 2010, Jan. 2011, 7:31-40.

World Health Organization, Epilepsy: Aetiology, Epidemiology and Prognosis, Fact Sheet No. 165, Feb. 2001 rev., printed Jan. 10, 2011, 4 pp.

Jun. 8, 2012 International Search Report in International Patent Application No. PCT/US12/26467 (international stage of U.S. Appl. No. 14/001,306).

Jun. 8, 2012 Written Opinion in International Patent Application No. PCT/US12/26467 (international stage of U.S. Appl. No. 14/001,306).

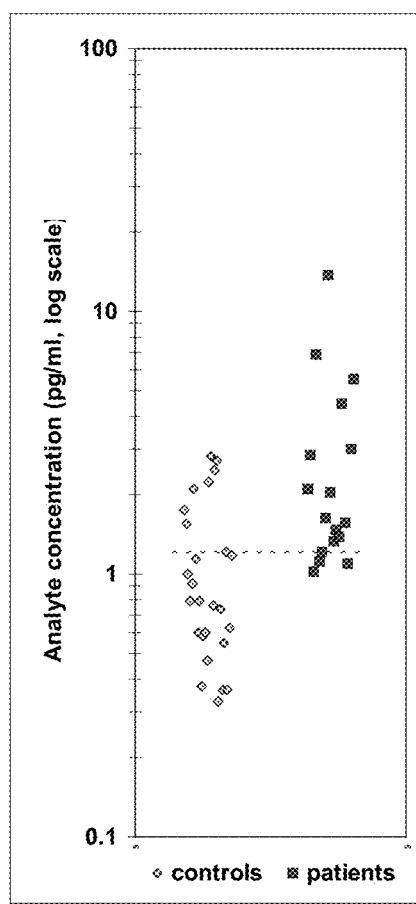
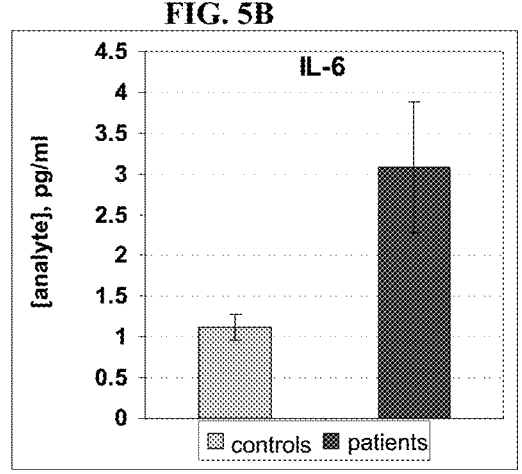
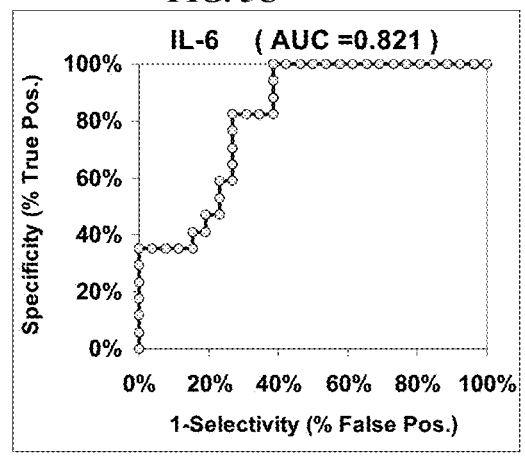
FIG. 5A
FIG. 5B
FIG. 5C

BIOMARKERS FOR SEIZURES

CROSS-REFERENCE TO RELATED APPLICATIONS

This application is a continuation of U.S. patent application Ser. No. 15/678,784, filed Aug. 16, 2017, which is a continuation of U.S. patent application Ser. No. 15/061,329, filed Mar. 4, 2016, now U.S. Pat. No. 9,772,335, issued Sep. 26, 2017, which is a continuation of U.S. patent application Ser. No. 14/943,101, filed Nov. 17, 2015 (now abandoned), which is a continuation of U.S. patent application Ser. No. 14/001,306, filed Aug. 23, 2013 (abandoned), which is a national stage of International Patent Application No. PCT/US2012/026467, filed Feb. 24, 2012 (expired), which claims the benefit of the priority of U.S. Provisional Patent Application No. 61/446,461, filed Feb. 24, 2011, which applications are incorporated herein by reference in their entireties.

BACKGROUND OF THE INVENTION

Epilepsy is presently characterized by at least two unprovoked seizures, although other definitions are evolving. It is currently estimated to affect 50 million people worldwide with 200,000 new cases diagnosed ever year in the United States alone. Current methods for diagnosing epilepsy are laborious and inaccurate. Differential diagnosis for epilepsy typically involves a neurological exam, patient history, neural imaging and electroencephalography (EEG). While EEGs are considered the most useful test in confirming a diagnosis of epilepsy, there are significant false positives from this test, and to a lesser extent, false negatives. Between 10% and 40% of people with epilepsy will have normal EEG results, even over several tests. The costs of the EEG may also not be understated, both in money and in time. No tests are available to determined imminent risk of seizure or risk of recurrence.

SUMMARY OF THE INVENTION

This application is directed toward a blood test for epilepsy diagnosis. The application provides individual and panels/arrays of biomarkers indicative of seizure or a tendency to have seizure. In one embodiment, a polypeptide expression panel or array is provided comprising a probe capable of binding soluble ICAM-5 (i.e., sICAM-5 or sICAM5) in blood plasma or blood serum of a mammalian subject, wherein a decreased plasma or serum concentration of sICAM-5 relative to a healthy control is indicative of seizure or a tendency to have seizure. Further panels comprise probes capable of binding TARC and/or IL-2, IL-6, IL-8, IL-1β, IFN-γ, and in combination with sICAM-5. Still further panels comprise probes capable of binding IL-10, IL-12 p70, Fas, Fas-ligand, MCP-1, MDC, MIP-10, GM-CSF, MCP-4, IL-10, BDNF, Eotaxin, Eotaxin-3, and/or TNF-α, and in combination with sICAM-5 and/or TARC.

Also provided are methods for detecting seizure, methods for assessing the effectiveness of a treatment of seizure, a tendency to have seizure, or treatment of an underlying disorder resulting in seizure, and diagnostic kits.

Other aspects and advantages of the present invention are described further in the following detailed description of the preferred embodiments thereof.

BRIEF DESCRIPTION OF THE DRAWINGS

FIG. 2A is a dot-plot of sICAM5 concentrations in plasma (◇, controls; □, patients). The dotted line is the cut-line that best discriminates between patients and controls. FIG. 2B is a bar graph and error calculation for data in FIG. 2A. Difference is significant for p=0.003. FIG. 2C is a ROC curve for data in FIG. 2A, showing an area under the curve (AUC) value of 0.803.

FIG. 3A is a dot-plot of TARC concentrations in plasma (◇, controls; □, patients). The dotted line is the cut-line that best discriminates between patients and controls. FIG. 3B is a bar graph and error calculation for data in FIG. 3A. Difference is significant for p=0.035. FIG. 3C is a ROC curve for data in FIG. 3A, showing an area under the curve (AUC) value of 0.759.

FIG. 4A is a dot-plot of TARC/sICAM5 concentration ratio in plasma (◇, controls; □, patients). The dotted line is the cut-line that best discriminates between patients and controls. FIG. 4B is a bar graph and error calculation for data in FIG. 4A. Difference is 17.1 fold, and is significant for p=0.025. FIG. 4C is a ROC curve for data in FIG. 4A, showing an area under the curve (AUC) value of 1.00.

FIGS. 5A-5C are charts summarizing an assay of IL-6 in plasma from epilepsy and control patients. FIG. 5A is a dot-plot of IL-6 concentrations in plasma (◇, controls; □, patients). The dotted line is the cut-line that best discriminates between patients and controls. FIG. 5B is a bar graph and error calculation for data in FIG. 5A. Difference is 2.8-fold, and is significant for p=0.012. FIG. 5C is a ROC curve for data in FIG. 5A, showing an area under the curve (AUC) value of 0.821.

FIG. 6A is a dot-plot of IL-6/sICAM5 concentration ratio in plasma (◇, controls; □, patients). The dotted line is the cut-line that best discriminates between patients and controls. FIG. 6B is a bar graph and error calculation for data in FIG. 6A. Difference is 9.9 fold, and is significant for p=0.05. FIG. 6C is a ROC curve for data in FIG. 6A, showing an area under the curve (AUC) value of 0.90.

FIG. 7A is a dot-plot of IL-8 concentrations in plasma (◇, controls; □, patients). The dotted line is the cut-line that best discriminates between patients and controls. FIG. 7B is a bar graph and error calculation for data in FIG. 7A. Difference is 1.4-fold, and significant for p=0.002. FIG. 7C is a ROC curve for data in FIG. 7A, showing an area under the curve (AUC) value of 0.715.

FIG. 8A is a dot-plot of IL-8/sICAM5 concentration ratio in plasma (◇, controls; □, patients). The dotted line is the cut-line that best discriminates between patients and controls. FIG. 8B is a bar graph and error calculation for data in FIG. 8A. Difference is 6.5-fold, and is significant for p=0.017. FIG. 8C is a ROC curve for data in FIG. 8A, showing an area under the curve (AUC) value of 0.88.

FIG. 9A is a dot-plot of IL-1β concentrations in plasma (◇, controls; □, patients). The dotted line is the cut-line that best discriminates between patients and controls. FIG. 9B is a bar graph and error calculation for data in FIG. 9A. Difference is significant for p=0.003. FIG. 9C is a ROC curve for data in FIG. 9A, showing an area under the curve (AUC) value of 0.803.

FIG. 10A is a dot-plot of IL-2 concentrations in plasma (◇, controls; □, patients). The dotted line is the cut-line that best discriminates between patients and controls. FIG. 10B is a bar graph and error calculation for data in FIG. 10A. Difference is significant for p=0.003. FIG. 10C is a ROC curve for data in FIG. 10A, showing an area under the curve (AUC) value of 0.788.

FIG. 11A is a dot-plot of IFN-γ concentrations in plasma (◇, controls; □, patients). The dotted line is the cut-line that best discriminates between patients and controls. FIG. 11B is a bar graph and error calculation for data in FIG. 11A. Difference is 2.4-fold, and significant for p=0.01. FIG. 11C is a ROC curve for data in FIG. 11A, showing an area under the curve (AUC) value of 0.701.

FIG. 12A is a dot-plot of GM-CSF concentrations in plasma (◇, controls; □, patients). The dotted line is the cut-line that best discriminates between patients and controls. FIG. 12B is a bar graph and error calculation for data in FIG. 12A. Difference is 1.2-fold, and significant for p=0.297. FIG. 12C is a ROC curve for data in FIG. 12A, showing an area under the curve (AUC) value of 0.554.

FIG. 13A is a dot-plot of BDNF concentrations in plasma (◇, controls; □, patients). The dotted line is the cut-line that best discriminates between patients and controls. FIG. 13B is a bar graph and error calculation for data in FIG. 13A. Difference is 1.1-fold, and significant for p=0.383. FIG. 13C is a ROC curve for data in FIG. 13A, showing an area under the curve (AUC) value of 0.527.

DETAILED DESCRIPTION OF THE INVENTION

Figure 1:
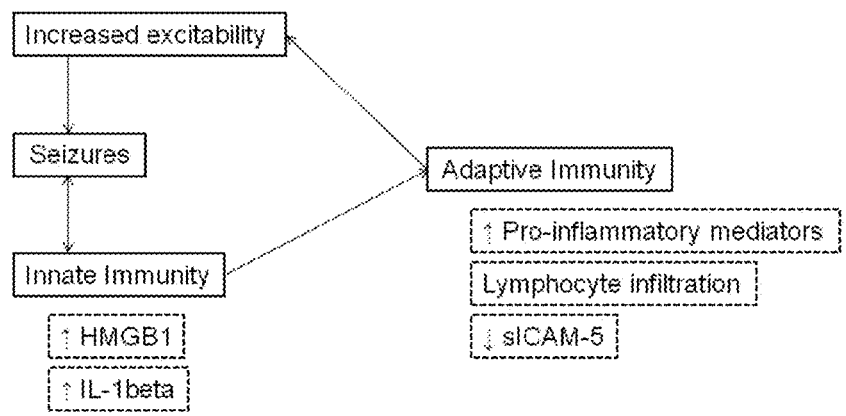
FIG. 1 is a model for inflammation and epilepsy.
Figure 2A:
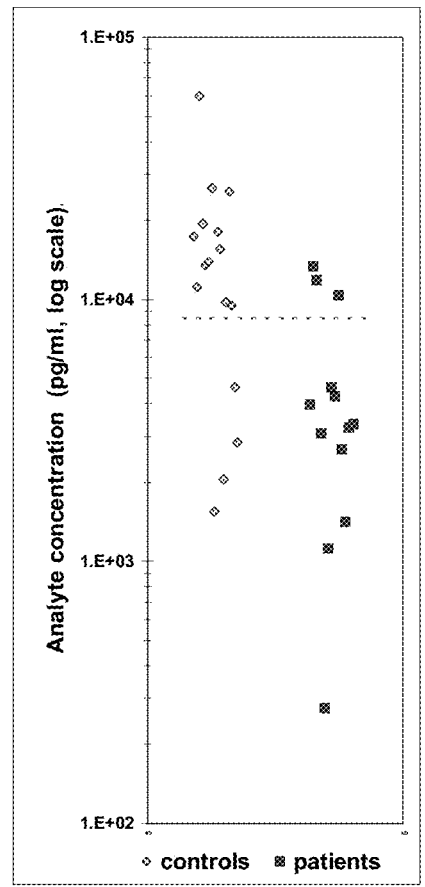
FIGS. 2A-2C are charts summarizing the assay of sICAM5 in plasma from epilepsy and control patients.
Figure 2B:
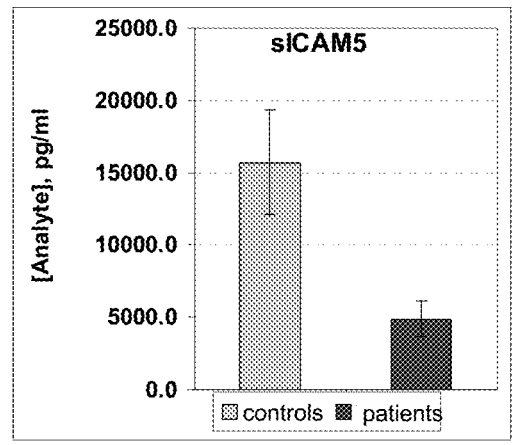
Figure 2C:
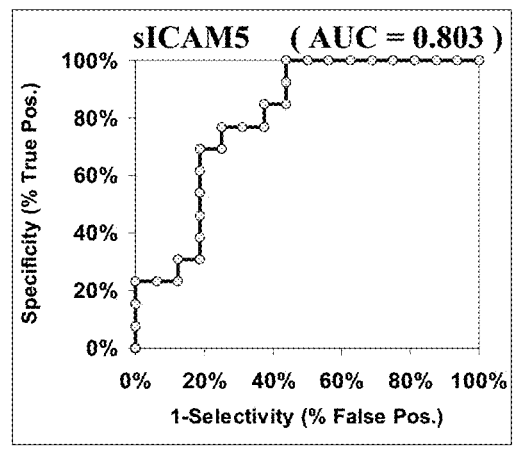
Figure 3A:
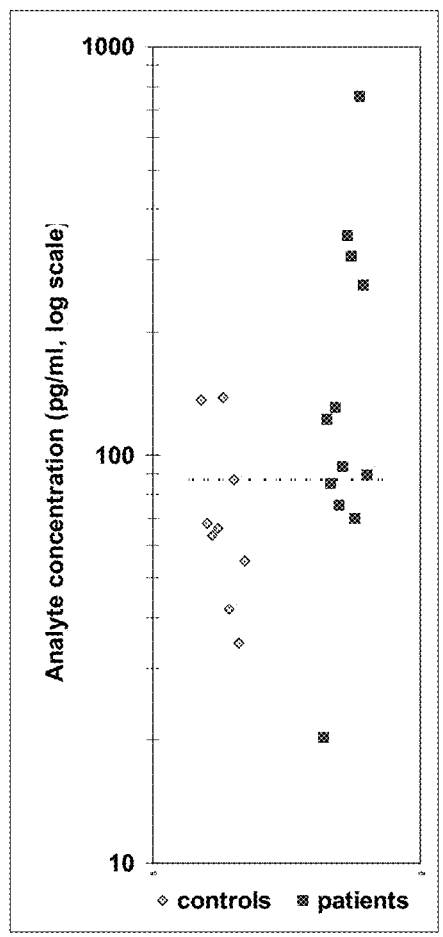
FIGS. 3A-3C are charts summarizing the assay of TARC in plasma from epilepsy and control patients.
Figure 3B:
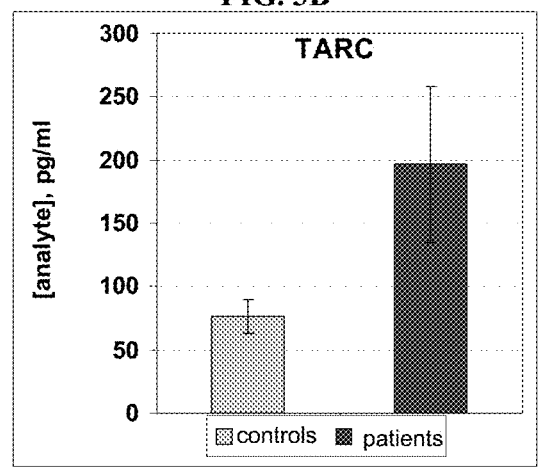
Figure 3C:
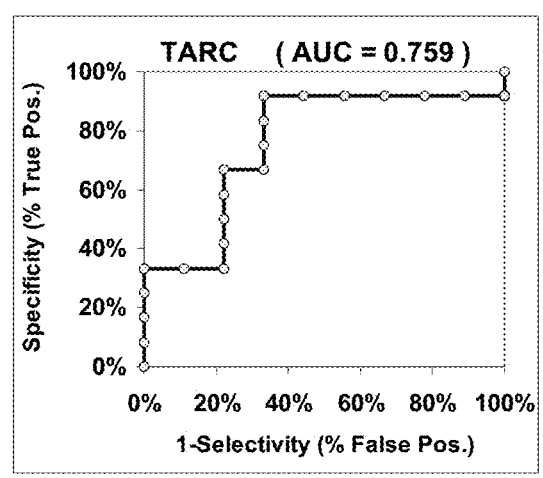
Figure 4A:
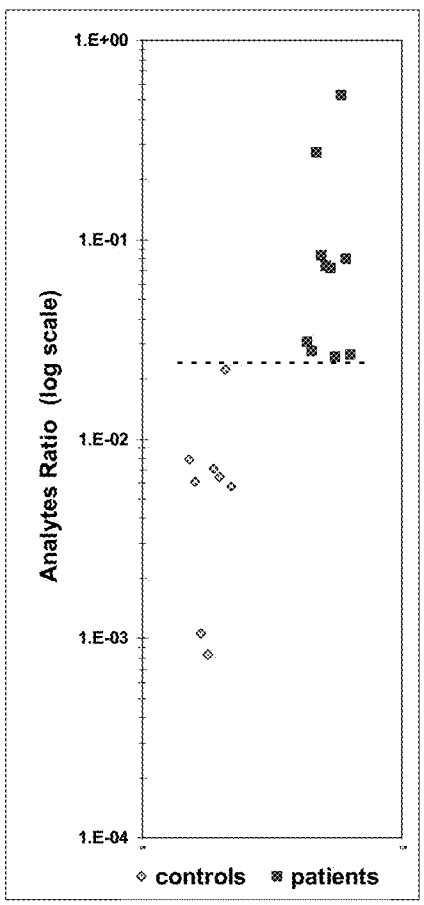
FIGS. 4A-4C are charts summarizing the assay of TARC/sICAM5 ratio in plasma from epilepsy and control patients.
Figure 4B:
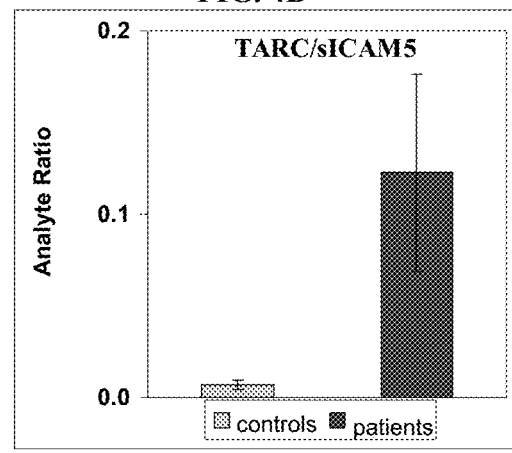
Figure 4C:
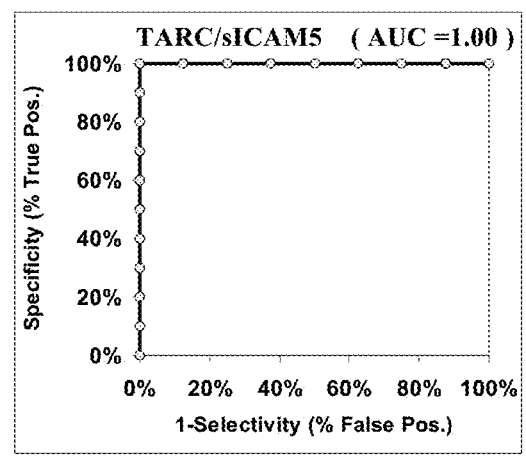
Figure 6A:
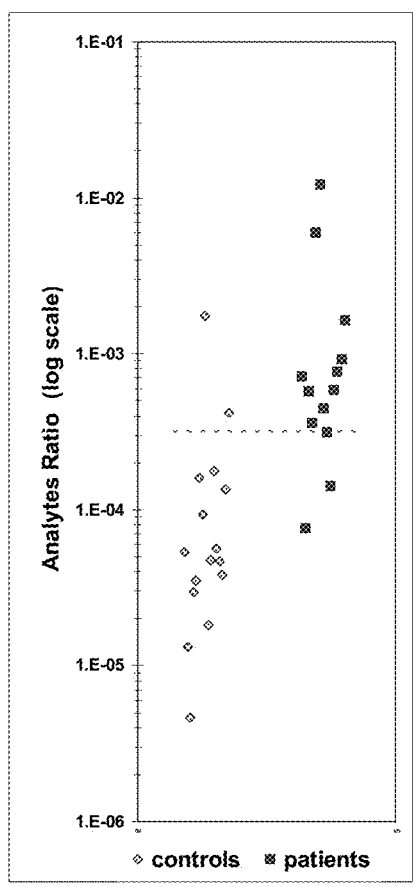
FIGS. 6A-6C are charts summarizing an assay of IL-6/sICAM5 ratio in plasma from epilepsy and control patients.
Figure 6B:
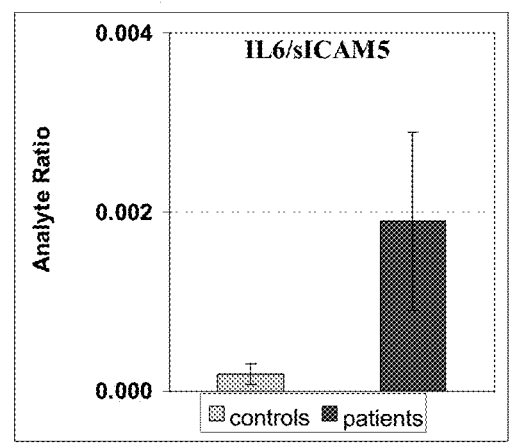
Figure 6C:
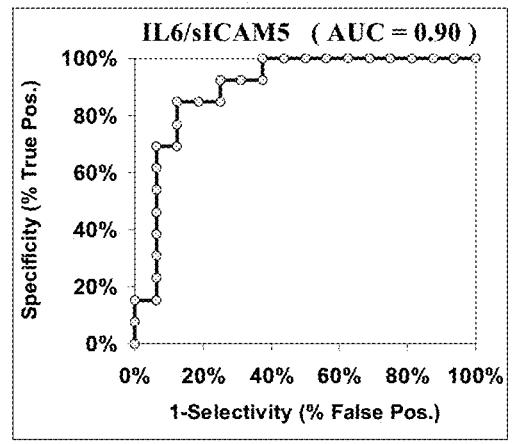
Figure 7A:
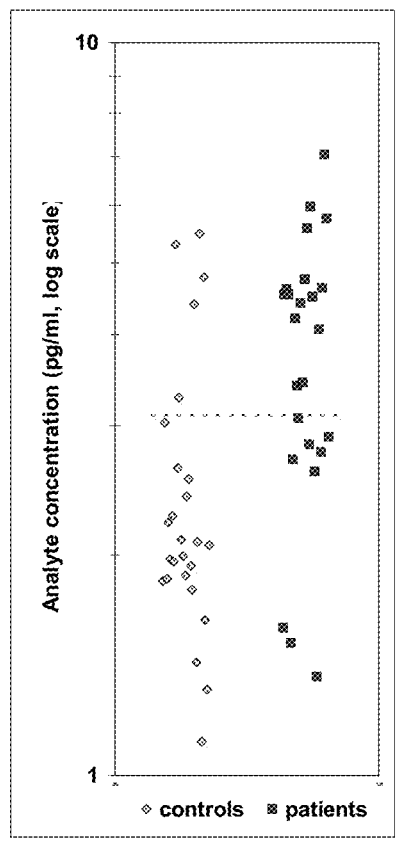
FIGS. 7A-7C are charts summarizing an assay of IL-8 in plasma from epilepsy and control patients.
Figure 7B:
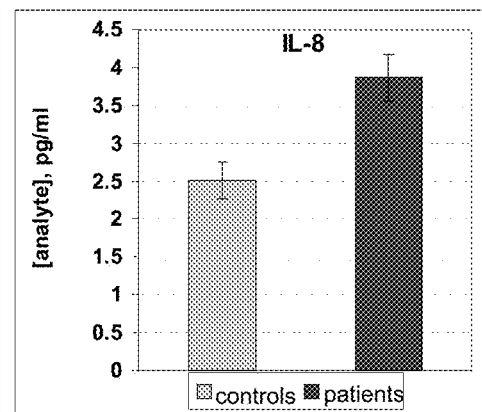
Figure 7C:
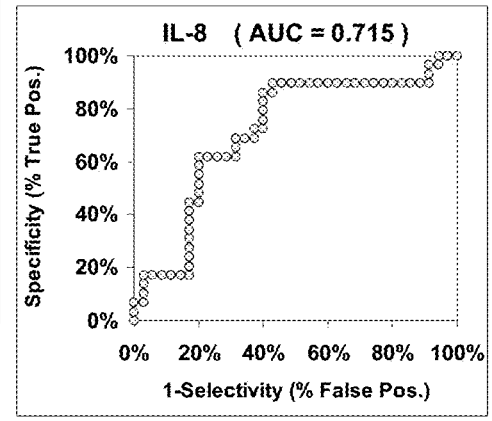
Figure 8A:
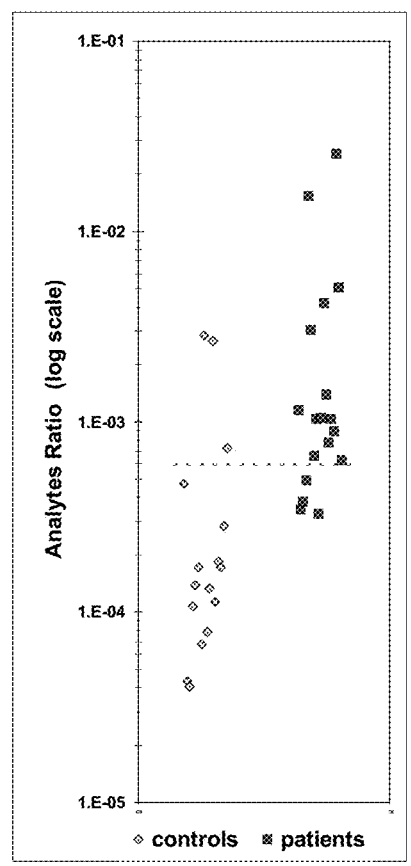
FIGS. 8A-8C are charts summarizing an assay of IL-8/sICAM5 ratio in plasma from epilepsy and control patients.
Figure 8B:
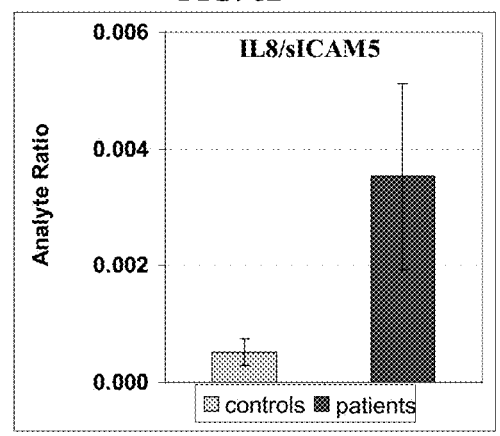
Figure 8C:
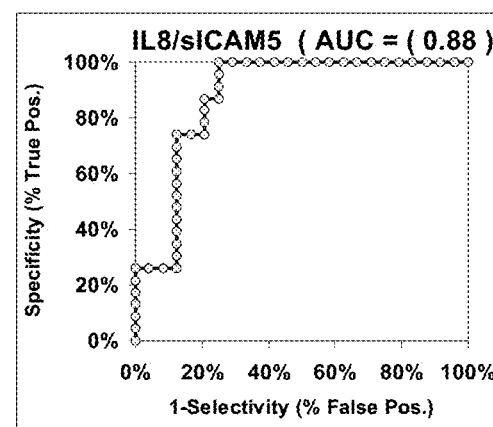
Figure 9A:
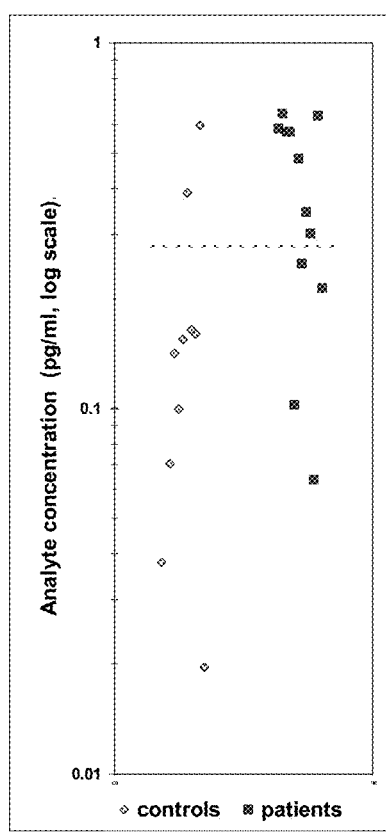
FIGS. 9A-9C are charts summarizing an assay of IL-1β in plasma from epilepsy and control patients.
Figure 9B:
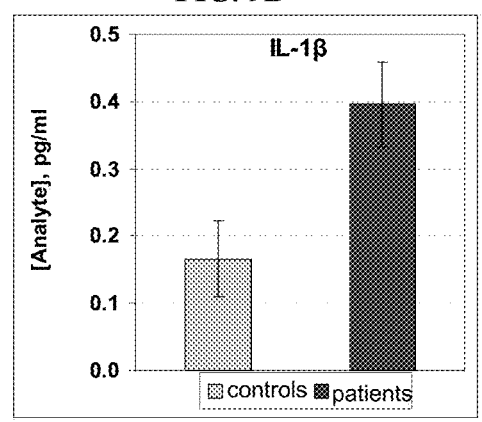
Figure 9C:
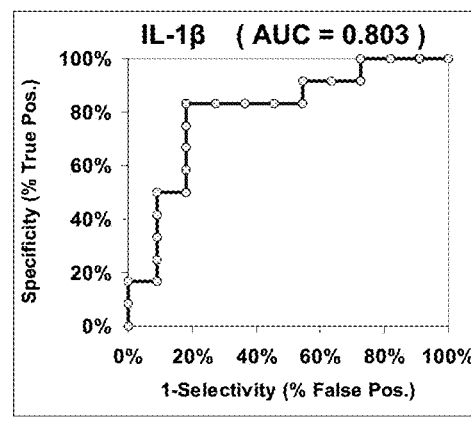
Figure 10A:
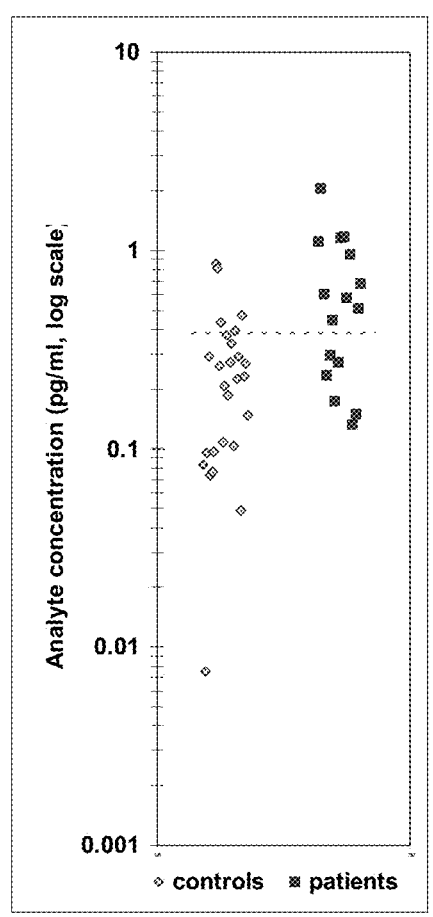
FIGS. 10A-10C are charts summarizing an assay of IL-2 in plasma from epilepsy and control patients.
Figure 10B:
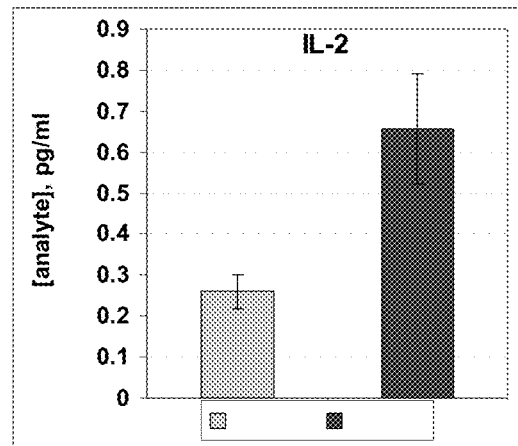
Figure 10C:
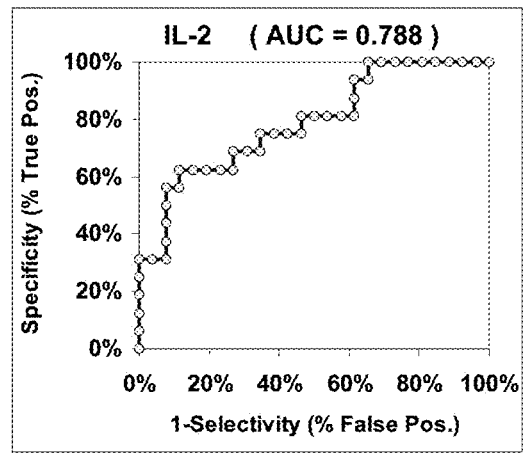
Figure 11A:
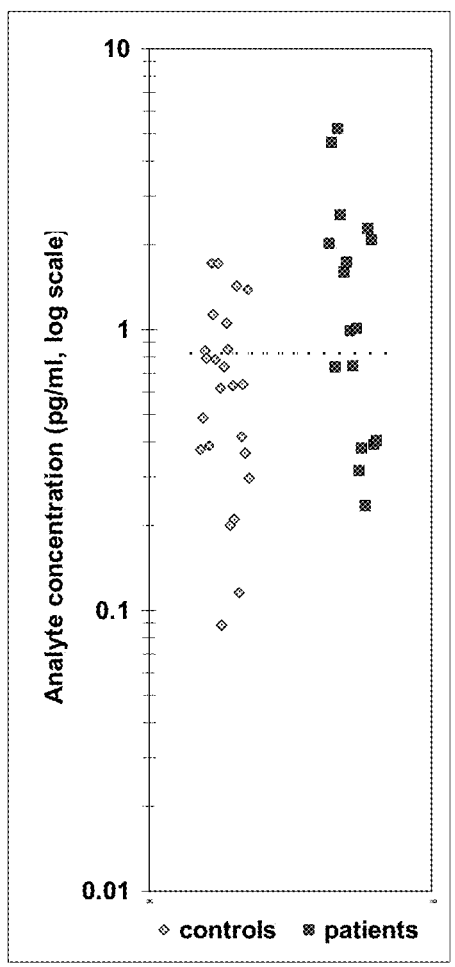
FIGS. 11A-11C are charts summarizing an assay of IFN-γ in plasma from epilepsy and control patients.
Figure 11B:
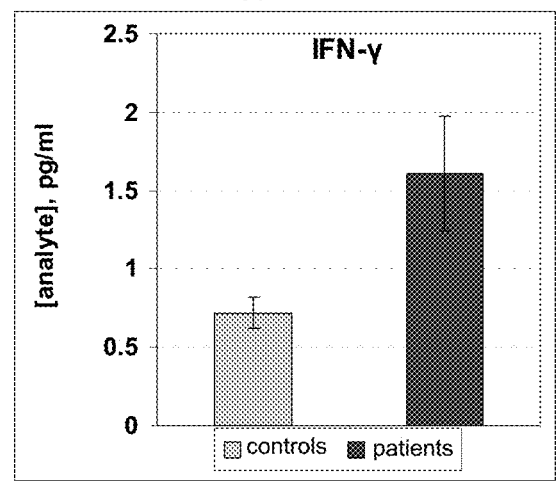
Figure 11C:
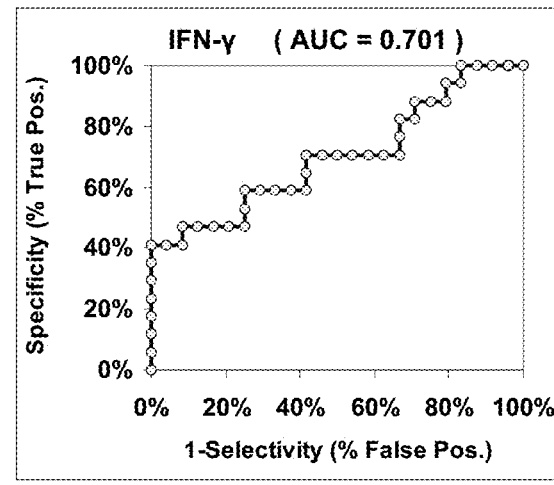
Figure 12A:
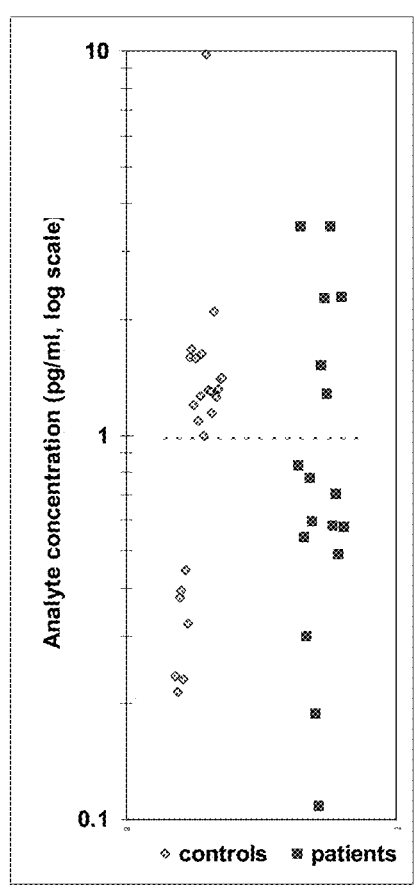
FIGS. 12A-12C are charts summarizing an assay of GM-CSF in plasma from epilepsy and control patients.
Figure 12B:
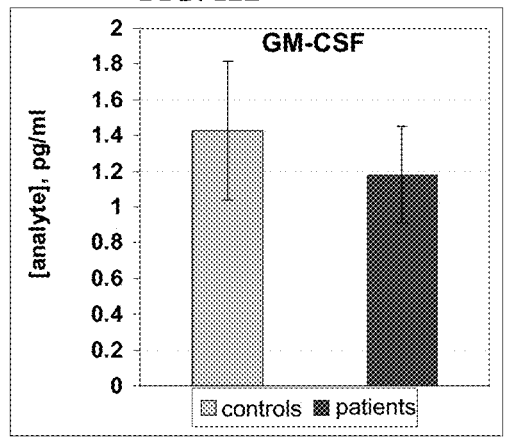
Figure 12C:
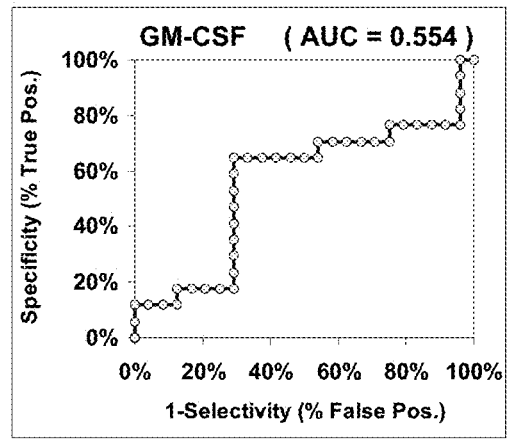
Figure 13A:
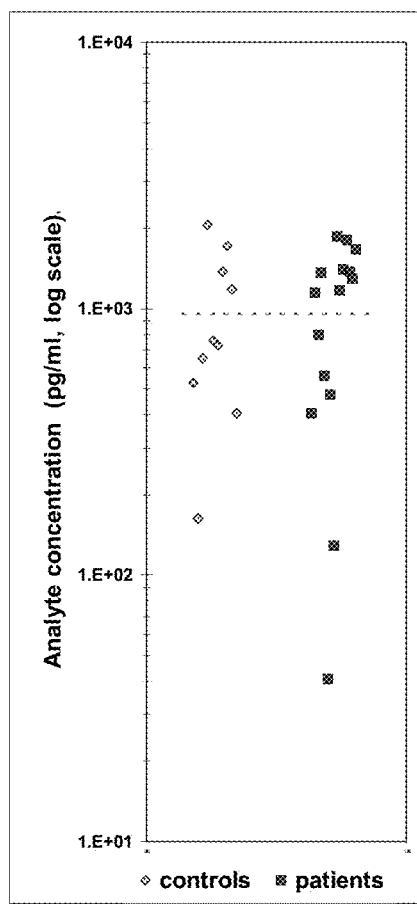
FIGS. 13A-13C are charts summarizing an assay of BDNF in plasma from epilepsy and control patients.
Figure 13B:
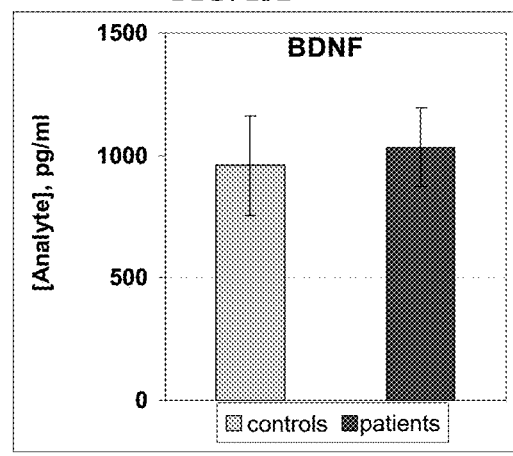
Figure 13C:
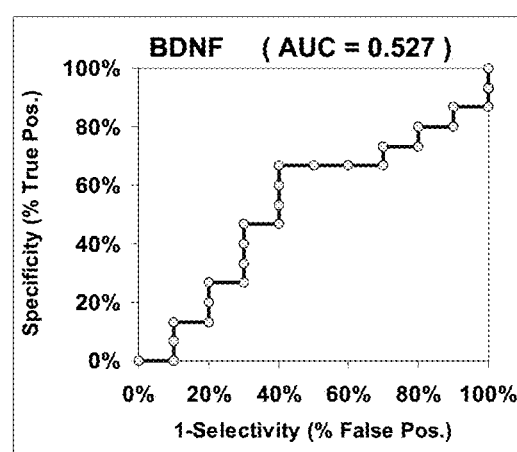

In many epilepsies, an immune response is generated within the region of seizure onset. In several distinct tissue lesion types such as tuberous sclerosis (TSC) and mesial temporal sclerosis (MTS), pro-inflammatory cytokines such as IL-1, IL-6, TNF-α, Fas, and Fas-ligand are activated. In addition, there is complement fixation and deposition, altered blood-brain barrier permeability, and macrophage infiltration. Inflammation may generate a wide variety of downstream effects including upregulation of IL-1β production, activation of TLR4, NFκB, mTOR, and MAPK cascades, attraction of activated lymphocytes, microglia, and macrophages, and alteration of astrocyte physiology. Without being bound by theory, these changes may be a result of a disease process leading to seizures, caused by seizures, and/or be the result of seizures (See FIG. 1). The present application addresses a need in the art for markers associated with seizures.

As used herein, the abbreviations "A1AT" and "α1AT" refer to alpha 1—antitrypsin, also known as serpin peptidase inhibitor, clade A (alpha-1 antiproteinase, antitrypsin), member 1.

The terms "comprising" and "including" are used interchangeably, unless otherwise noted.

The term "cryptogenic" is used herein to refer to a seizure or epilepsy of unknown origin.

The terms "disease", "disorder", or "condition" are used herein to refer to any manifestations, symptoms, or combination of manifestations or symptoms, recognized or diagnosed as leading to, causing, or influencing seizure. The terms include, but are not limited to, traumas, inflammatory and autoimmune responses, physiological malformations, and genetic defects.

The abbreviation "GM-CSF" refers to granulocyte-macrophage colony-stimulating factor.

The abbreviation "HGF" refers to hepatocyte growth factor.

The abbreviation "ICAM-1" refers to intercellular adhesion molecule 1.

The term "ictal" refers to a physiologic state or event such as a seizure. The term "indicative" (or "indicative of") encompasses both prediction (including tendency), and detection (proximate to the occurrence of a seizure), and unless otherwise noted, embodiments encompassing the term are intended to define and encompass embodiments specific to prediction, specific to detection, and for prediction as well as for detection of a past or current event. Use of the term indicative in conjunction with the term "tendency" is intended solely for emphasis of evidence of a past event versus a tendency toward a future event, but the use solely of indicative is intended to encompass tendency unless otherwise indicated.

The abbreviation "BDNF" refers to brain-derived neurotrophic factor.

The abbreviation "MCP-1" refers to monocyte chemotactic protein-1, also known as chemokine (C-C motif) ligand 2 (CCL2), or variants thereof.

The abbreviation "MDC" refers to macrophage derived chemokine, also known as C-C motif chemokine 22 (CCL-22), or variants thereof.

The abbreviation "MIP-1β" refers to macrophage inflammatory protein-1β, also known as chemokine C-C motif ligand 4 (CCL-4), or variants thereof.

The abbreviation "IP-10" refers to interferon gamma-induced protein 10, small-inducible cytokine B10, C-X-C motif chemokine 10 (CXCL10), or variants thereof.

Eotaxin, also known as eotaxin-1, refers to chemokine (C-C motif) ligand 11 (CCL11), or variants thereof.

Eotaxin-3 refers to chemokine (C-C motif) ligand 26 (CCL26), or variants thereof.

The term "sample" is used herein to refer to a blood plasma or blood serum sample, unless otherwise noted. In each embodiment described herein, the use of blood plasma is contemplated as an independent embodiment from the alternative of blood plasma or blood serum. In each embodiment described herein, the use of blood serum is contemplated as an independent embodiment from the alternative of blood plasma or blood serum. In each embodiment described herein, the use of another biological sample, including but not limited to cerebrospinal fluid (CSF) and a tissue sample obtained by resection, is contemplated according to conventional techniques in the art for obtaining the sample and for analysis of same. The sample can be treated prior to use, such as preparing plasma from blood, diluting viscous fluids, and the like. Methods of treatment can involve filtration, distillation, extraction, concentration, inactivation of interfering components, the addition of reagents, and the like.

The terms "seizure" and "epilepsy" are used interchangeably, two unprovoked seizures being required for a clinical diagnosis of epilepsy, unless otherwise noted. The term epilepsy may also be defined by the understanding of, or theories of, seizure as understood as of the filing of the application.

The terms "subject", "individual", and "patient" are used interchangeably herein to refer to a mammal from which a sample is taken, unless otherwise noted. The terms are intended to encompass embodiments specific to humans. A subject, individual or patient may be afflicted with, at risk for, or suspected of having a tendency to have seizure or a disorder for which seizure is symptomatic. The term also includes domestic animals bred for food or as pets, including horses, cows, sheep, pigs, cats, dogs, and zoo animals. Typical subjects for treatment include persons susceptible to, suffering from or that have suffered one or more seizures. In particular, suitable subjects for treatment in accordance with the invention are persons that are susceptible to or that have suffered one or more seizures.

The abbreviation "TARC" refers to 'thymus and activation regulated chemokine', and is used interchangeably herein with chemokine (C-C motif) ligand 17 (CCL17).

The terms "telencephalin", "TLN", "ICAM-5", and "ICAM5" are used interchangeably herein.

The term "tendency", e.g., "tendency to have seizure", is intended to refer to a reasonable medical probability of an event, e.g., seizure to occur or recur. The term also encompasses the frequency with which such events may occur before, after, or during ongoing treatment.

As used herein, the term "treat" or "treating" refers to any method used to partially or completely alleviate, ameliorate, relieve, inhibit, prevent, delay onset of, reduce severity of and/or reduce incidence of one or more symptoms or features of a particular condition, e.g., seizure or a seizure-related disorder. Treatment may be administered to a subject who does not exhibit signs of a condition and/or exhibits only early signs of the condition for the purpose of decreasing the risk of developing pathology associated with the condition. Thus, depending on the state of the subject, the term in some aspects of the invention may refer to preventing a condition, and includes preventing the onset, or preventing the symptoms associated with a condition. The term also includes maintaining the condition and/or symptom such that the condition and/or symptom do not progress in severity. A treatment may be either performed in an acute or chronic way. The term also refers to reducing the severity of a condition or symptoms associated with such condition prior to affliction with the condition. Such prevention or reduction of the severity of a condition prior to affliction refers to administration of a therapy to a subject that is not at the time of administration afflicted with the condition. Preventing also includes preventing the recurrence of a condition, frequency thereof, or of one or more symptoms associated with such condition. The terms "treatment" and "therapeutically" refer to the act of treating, as "treating" is defined above. The purpose of intervention is to combat the condition and includes the administration of therapy to prevent or delay the onset of the symptoms or complications, or alleviate the symptoms or complications, or eliminate the condition. For example, a treatment may be used to ameliorate symptoms or frequency thereof (e.g., frequency of seizure) associated with a disorder.

The terms "tuberous sclerosis", "tuberous sclerosis complex", and the abbreviation/acronyms "TS" and "TSC", are used interchangeably herein.

The abbreviation "VCAM-1" refers to vascular cell adhesion molecule 1.

The abbreviation "VEGF-A" refers to vascular endothelial growth factor A.

In one embodiment, a polypeptide expression panel or array is provided, the panel or array comprising a probe capable of binding soluble ICAM-5 (sICAM-5) in blood plasma or blood serum of a mammalian subject, wherein a decreased plasma or serum concentration of sICAM-5 relative to a healthy control is indicative of seizure or a tendency to have seizure. In another embodiment, a polypeptide expression panel or array is provided, the panel or array comprising a probe capable of binding TARC in blood plasma or blood serum of a mammalian subject, wherein an increased plasma or serum concentration of TARC relative to a healthy control is indicative of seizure or a tendency to have seizure.

Also provided is a polypeptide or array comprising a probe capable of binding sICAM-5 in blood plasma or blood serum and a probe capable of binding TARC in blood plasma or blood serum of a mammalian subject, wherein a decreased plasma or serum concentration of sICAM-5 in combination with an increased plasma or serum concentration of TARC (relative to a healthy control) indicates seizure or a tendency to have seizure. In further embodiments, the increase of the ratio of TARC/sICAM-5 in tested subjects relative to control (healthy, non-epileptic/non-seizure) is greater than 20, greater than 17, greater than 15, greater than 10, greater than 5, or greater than 1. The ratio may also be 2, 3, 4, 5, 6, 7, 8, 9, 10, 11, 12, 13, 14, 15, 16, 17, 18, 19, 20, or fractional increments thereof, e.g. 1.4 and 1.5. In other embodiments, the ratio is 2 or more whole or fractional standard deviations above the mean for controls.

The above panels or arrays may also include one or more probes capable of binding one or more of IL-2, IL-6, IL-8, IL-1β, and IFN-γ, wherein an increased plasma or serum concentration of one or more relative to a healthy control is indicative of seizure or a tendency to have seizure.

In still further embodiments, the polypeptide expression panel or arrays described above may further include one or more probes capable of binding IL-10, IL-12 p70, Fas, Fas-ligand, MCP-1, MDC, MIP-1β, GM-CSF, MCP-4, IP-10, BDNF, Eotaxin-3, Eotaxin, and TNF-α, wherein an altered plasma or serum concentration of one or more of IL-10, IL-12 p70, Fas, Fas-ligand, MCP-1, MDC, MIP-1β, GM-CSF, MCP-4, IP-10, BDNF, Eotaxin-3, Eotaxin, and TNF-α (relative to a healthy individual) indicates a tendency to have seizure. In further embodiments, the patient is a human.

In another embodiment, a method for predicting or detecting seizure is provided, comprising contacting a blood plasma or blood serum sample obtained from a mammalian subject with a diagnostic reagent that can measure or detect the expression level of soluble ICAM-5 (sICAM-5) and contacting a blood plasma or blood serum sample obtained from a mammalian subject with a diagnostic reagent that can measure or detect the expression level of TARC, wherein a decreased plasma or serum concentration of sICAM-5 relative to a healthy control in combination with an increased plasma or serum concentration of TARC indicates a seizure having occurred or a tendency to have seizure.

The method may also include contacting the blood plasma or blood serum sample with one or more diagnostic reagents that can measure or detect the expression level of IL-2, IL-6, IL-8, IL-1β, and IFN-γ, wherein altered plasma or serum concentration of one or more of IL-2, IL-6, IL-8, IL-1β, and IFN-γ relative to a healthy control indicates a tendency to have seizure. Still further the method may include contacting the blood plasma or blood serum sample with a diagnostic reagent that can measure or detect the expression level of one or more diagnostic reagents that can measure or detect the expression level of IL-10, IL-12 p70, Fas, Fas-ligand, MCP-1, MDC, MIP-1β, GM-CSF, MCP-4, IP-10, BDNF, Eotaxin-3, Eotaxin, and TNF-α, wherein altered plasma or serum concentration of one or more of IL-10, IL-12 p70, Fas, Fas-ligand, MCP-1, MDC, MIP-1β, GM-CSF, MCP-4, IP-10, BDNF, Eotaxin-3, Eotaxin, and TNF-α relative to a healthy control indicates a seizure having occurred or a tendency to have seizure.

In yet another embodiment, a method for assessing the effectiveness of a treatment of seizure or a disorder for which seizure is symptomatic is provided, the method including contacting a first blood plasma or blood serum sample obtained from a mammalian subject prior to treatment with one or more diagnostic reagents that can measure or detect the expression level of soluble ICAM-5 (sICAM-5) and/or TARC, and contacting a second blood plasma or blood serum sample obtained from a mammalian subject subsequent to treatment with a diagnostic reagent that can measure or detect the expression level of soluble ICAM-5 (sICAM-5) and/or TARC, wherein an increased plasma or serum concentration of sICAM-5 and/or a decreased level of TARC in the second blood plasma or blood serum sample relative to the first blood plasma or blood serum sample indicates effectiveness in treatment of seizure or a disorder for which seizure is symptomatic. The method may further include contacting the first blood plasma or blood serum sample and the second blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and TNF-α in the second blood plasma or blood serum sample relative to the first blood plasma or blood serum sample indicates effectiveness in treatment of seizure or a disorder for which seizure is symptomatic.

In still further embodiments, a method for determining the whether or not one or more seizures are resultant from inflammation, comprising contacting a blood plasma or blood serum sample obtained from a mammalian subject with a diagnostic reagent that can measure or detect the expression level of soluble ICAM-5 (sICAM-5) and/or contacting a blood plasma or blood serum sample obtained from a mammalian subject with a diagnostic reagent that can measure or detect the expression level of TARC, wherein a decreased plasma or serum concentration of sICAM-5 relative to a healthy control and/or an increased plasma or serum concentration of TARC indicates an inflammatory basis or component of seizure. The method may further include contacting the blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and TNF-α in the blood plasma or blood serum sample indicates an inflammatory basis or component of seizure.

In yet other embodiments, a method for determining the whether or not seizure is likely to occur in a subject is provided, comprising contacting a blood plasma or blood serum sample obtained from a mammalian subject with a diagnostic reagent that can measure or detect the expression level of soluble ICAM-5 (sICAM-5) and/or contacting a blood plasma or blood serum sample obtained from a mammalian subject with a diagnostic reagent that can measure or detect the expression level of TARC, wherein a decreased plasma or serum concentration of sICAM-5 relative to a healthy control and/or an increased plasma or serum concentration of TARC indicates a tendency to have seizure. The method may further include contacting the blood plasma or blood serum sample with one or more diagnostic reagents that can measure or detect the expression level of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and TNF-α, wherein an altered concentration of IL-6, IL-8, IL-2, IL-1β, IFN-γ, IL-10, IL-12 p70, Fas, Fas-ligand, MCP-1, MDC, MIP-1β, GM-CSF, MCP-4, IP-10, BDNF, Eotaxin-3, Eotaxin, and TNF-α in the blood plasma or blood serum sample indicates a tendency to have seizure.

In specific further embodiments of the above, the seizure is associated with a temporal lobe epilepsy. In a further embodiment, the temporal lobe epilepsy is mesial temporal sclerosis (MTS). In other embodiments, the seizure is associated with tuberous sclerosis complex (TSC).

In still other specific further embodiments of the above, the seizure may be cryptogenic. In further embodiments, the seizure is not associated with immune response to a pathogen.

The embodiments, including the probes and panels/arrays of probes, described herein may be used to detect whether or not a seizure has (is likely to have occurred). They may also be used to predict the likelihood of further seizure. Additionally, they may be used to predict whether or not seizure is likely following a brain injury or head trauma. They are also useful in identifying whether or not a seizure is the result of an inflammatory process. Further, they may be used in assessing whether or not a treatment is effective.

ICAM-5 is a neuron-derived protein differentially distributed in the blood plasma or blood serum of epilepsy patients relative to healthy patients. Soluble ICAM-5 (also known as sICAM5, sICAM-5, or variants thereof) is cleaved from ICAM-5 by metalloproteases in response to inflammation. Unexpectedly, it is found that decreased sICAM-5 expression is found in the case of seizure patients relative to healthy patients. As reflected in Example 1 herein, sICAM-5 expression is a diagnostic marker better than any presently available. Further, as reflected in Table 4 (see Example 3) herein, other markers are also indicative of a tendency to have seizure.

TARC is also an effective marker, differentially distributed in the blood plasma or blood serum of epilepsy patients relative to healthy patients and it is shown to be elevated in seizure patients. In combination, the TARC/sICAM-5 ratio is significantly elevated (ratio of 17.1) over healthy control. Additional markers that are useful include, alone or in combination, IL-1β, IL-2, IL-8, and IFN-γ. Still additional markers that are useful include, alone or in combination, IL-10, IL-12 p70, Fas, Fas-ligand, MCP-1, MDC, MIP-1β, GM-CSF, MCP-4, IP-10, BDNF, Eotaxin-3, Eotaxin, and TNF-α. Probes may further include α1AT, VCAM-1, ICAM-1, HGF, and VEGF-A. Probes may also include those for components of the complement cascade, e.g., C1q, C3c and C3d.

By way of non-limiting example, the following polypeptide panels or arrays are embodiments of the application (the terms decreased, elevated, and altered refer to the expression level in the epileptic patient versus that in a healthy subject):

sICAM-5 (decreased);
sICAM-5 (decreased), TARC (increased);
sICAM-5 (decreased), TARC (increased), IL-1β (increased), IL-6 (increased), IL-8 (increased);
sICAM-5 (decreased), TARC (increased), IL-1β (increased), IL-2 (increased), IL-6 (increased), IL-8 (increased), IFN-γ (increased);
sICAM-5, GM-CSF, BDNF;
sICAM-5, GM-CSF, BDNF, IL-1β;
sICAM-5, IL1β, IL-6;
sICAM-5, BDNF, IL-12 p70;
GM-CSF, BDNF;
GM-CSF, BDNF;
sICAM-5, GM-CSF, IFN-γ, IL-10, IL-12 p70, IL-1β, IL-2, IL-6, IL-8, TNF-α;
sICAM-5, GM-CSF, BDNF, IFN-γ, IL-10, IL-12 p70, IL-1β, IL-2, IL-6, IL-8, TNF-α;
GM-CSF, IFN-γ, IL-10, IL-12 p70, IL-1β, IL-2, IL-6, IL-8, TNF-α;
GM-CSF, BDNF, IFN-γ, IL-10, IL-12 p70, IL-1β, IL-2, IL-6, IL-8, TNF-α; and
sICAM-5, TARC, IL-1β, IL-2, IL-8, IFN-γ IL-10, IL-12 p70, Fas, Fas-ligand, MCP-1, MDC, MIP-1β, GM-CSF, MCP-4, IP-10, BDNF, Eotaxin-3, Eotaxin, TNF-α.

Also provided is a diagnostic kit comprising a polypeptide expression panel or array as described herein. The kit may also be predictive, useful in determining imminent risk of seizure or recurrence of seizure, or in assessing recurrence risk. In one embodiment, the kit is for the diagnosis of a temporal lobe epilepsy, such as MTS. In another embodiment, the kit is for the diagnosis of tuberous sclerosis complex (TSC). The kit may also contain a syringe and/or vile for drawing blood. The kit will contain one or more probes corresponding to the polypeptide markers of the panel or array. The kit may also an ELISA plate. A multiple and portable (M&P) ELISA may also be provided as part of a kit of an embodiment. Still other suitable components will be known to one of skill in the art, and are encompassed hereby.

Samples may be obtained from patients by conventional techniques. These techniques may include those covered by an institutional review board (IRB) approved protocol. In one embodiment, the samples are anticoagulated using sodium citrate. In a further embodiment, plasma is prepared by centrifuging samples, e.g., at 5,000 g (g=gravity) for 15 minutes at 4° C. Controls may also be purchased from commercial vendors.

Levels (concentrations) of the polypeptide to be quantified in plasma may be obtained by any of a number of methods known in the art, the particular procedure not being a limitation of the embodiments herein. For example, ELISA, Indirect ELISA, Sandwich ELISA, Competitive Elisa, and Multiple and Portable (M&P) ELISA may be used. Probes specific to the antigen (polypeptide or marker) to be detected may be obtained commercially or designed by techniques known in the art. In one embodiment for sICAM-5 detection, protein G affinity purified mouse monoclonal anti-human ICAM-5 antibody is used as the capture antibody. Single- and Multi-probe kits are available from commercial suppliers, e.g., Meso Scale Discovery. These kits include the kits referenced in the Examples hereto.

Also described herein are methods of treating or preventing seizure or a disorder for which seizure is symptomatic in a mammalian subject, comprising delivery of sICAM-5. In a further embodiment, the mammal is a human. Also provided is use of sICAM-5 to treat or prevent seizure or a disorder for which seizure is symptomatic in a mammalian subject, and use in preparing a medicament therefor. Given that ICAM-5 is expressed on the surface of telencephalic neurons (i.e., is localized to the brain), treatment or prevention may be effected without undesired systemic effects.

Treatment or prevention may be made intravenous or via intra-cerebrospinal fluid (intra-CSF) by techniques known to one of skill in the art. Delivery may also be made by any other suitable means, including by intranasal delivery to the CSF with a suitable carrier or excipient.

EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein. The specific embodiments described in the Examples are intended to be embodiments of the invention.

Example 1—Evaluation of ICAM5, TARC, and Other Polypeptides (Alone and in Combination) as Blood Plasma Markers of Seizure or a Tendency Therefor Sample Collection and Processing Blood samples are collected from human epilepsy patients. The samples are anticoagulated using Na-citrate, and the plasma is prepared by centrifuging samples at 5,000×G for 15 minutes at 4° C. The supernatant solutions are then aliquoted and stored at −80° C. Following centrifugation, the supernatant solutions are aliquoted and frozen at −80° C. Samples of plasma, also anticoagulated with Na-citrate, are purchased from commercial vendors. Differences among sets of controls are not significant where p>0.05.

Detection/Quantification of sICAM-5

Levels of immunoreactive Telencephalin/ICAM-5 in plasma were measured by sandwich ELISA using electrochemiluminescence detection. Assays were carried out on high bind SECTOR® Imager 6000 reader plates (Meso Scale Discovery (MSD), Gaitherburg, Md.) as follows. Wells were coated overnight with protein G affinity purified mouse monoclonal anti-human ICAM-5 antibody (capture antibody; R&D Systems, Minneapolis, Minn.; catalog #MAB 1950), 2 µg/ml diluted in phosphate buffered saline (PBS) (25 µL/well). Wells were emptied and then blocked for two hours with 10% fetal bovine serum (FBS; Invitrogen, Carlsbad, Calif.) in PBS (PBS-10% FBS). Wells were washed 3× with PBS containing 0.05% tween-20 (PBS-T) and samples were introduced into the wells in a total volume of 100 µL consisting of 25 µL human plasma and 75 µL PBS-5% FBS. ICAM-5 standard curves were prepared similarly in buffer containing 25 µL equine plasma (human ICAM-5-free) (Invitrogen, Carlsbad, Calif.), to control for the effects of sample matrix. Plates were incubated for three hours, washed and then incubated for one hour with biotinylated goat anti-human ICAM-5 antibody purified by human ICAM-5 affinity chromatography (R&D Systems; catalog #BAF1950; 1 µg/ml in PBS-1% FBS; 25 µL/well). Plates were washed and reacted for one hour with MSD®

SULFO-TAG labeled streptavidin detection reagent (Meso Scale Discovery; catalog #R32AD; 1 µg/ml in PBS containing 1% bovine serum albumin (BSA); 25 µL/well). Plates were washed, treated with the addition of MSD Read Buffer (Meso Scale Discovery; catalog #R92TC; 150 µL/well) and electrochemiluminescence read using a SECTOR® Imager 6000 instrument (Meso Scale Discovery). All incubations were carried out at room temperature with the exception of that for the capture antibody which was carried out at 4° C. The assay was sensitive to less than 0.34 ng/ml as defined by the electrochemiluminescence signal value that was 10 times the standard deviation above the mean electrochemiluminescence signal recorded for the 0 ng ICAM-5 standard (N=10).

Detection/Quantification of BDNF

Levels of immunoreactive BDNF in plasma were measured in a manner similar to sICAM-5 (Example 1) using antibodies and BDNF standard protein provided in the R&D Systems human BDNF ELISA Development Kit (catalog #DY248, Meso Scale Discovery). Detection is by electrochemiluminescence using the MSD® SULFO-TAG labeled streptavidin detection reagent and SECTOR® Imager 6000 instrument (Meso Scale Discovery). The assay is sensitive to less than 0.08 ng/ml as defined by the electrochemiluminescence signal value that was 10 times the standard deviation above the mean electrochemiluminescence signal recorded for the 0 ng BDNF standard (N=10).

Detection/Quantification of Other Polypeptides

Two multiplexed assays for cytokines and chemokines were used for analysis of patient and control plasma samples on the SECTOR® Imager 6000 instrument (Meso Scale Discovery, Gaithersburg, Md.) The first of these assays is the HUMAN PROINFLAMMATORY 9 PLEX™ Assay for the measurement of IL-2, IL-8, IL-12p70, IL-1β, GM-CSF, IFN-γ, IL-6, IL-10 and TNF-α (MesoScale catalog #K15007C-4). The second of these assays is the HUMAN CHEMOKINE 9 PLEX™ Assay for the measurement of Eotaxin, MIP-1β, Eotaxin-3, TARC, IP-10, IL-8, MCP-1, MDC, and MCP-4 (catalog #K15001C-1). The samples are added to plates that were pre-coated with capture antibodies for the specific cytokines. The plates was sealed and shaken at room temperature for two hours. The plates were washed in PBS+0.05% Tween-20 and detection antibody solution (1× or 1 µg/mL) is added. The plates were once again sealed and set to shake at room temperature for two hours. The plates were then washed once more in PBS+0.05% Tween-20. Read buffer was added at a 2× concentration and the plate was read on the SECTOR® 6000 Imager.

Other assays prepared by one of skill in the art or commercially available are used for additional polypeptides.

Results

Human epilepsy patient samples had altered levels of one or more polypeptides relative to control. Data is reflected in Table 1, below, and in FIGS. 2A-2C through 13A-13C. The data is described in the BRIEF DESCRIPTION OF THE DRAWINGS, above. Analyzed with a Receiver Operating Characteristic/Condition (ROC) calculation, the area under the curve (AUC), which is a measure of how well the assay detects epilepsy, was 0.70 or greater where p≤0.05 (an AUC value of 1.0 would reflect a perfect diagnostic).

TABLE 1

| Analyte | Epilepsy[1] | Epilepsy n | Controls[1] | Controls n | Ratio[2] | p-value[3] | AUG[4] |
|---|---|---|---|---|---|---|---|
| IL-1β | 0.3 ± 0.1 | 12 | 0.1 ± 0.0 | 10 | ↑ 4.0 | 0.003 | 0.80 |
| sICAM5 | 4.24 ± 1.14 (ng/ml) | 13 | 15.72 ± 3.63 (ng/ml) | 16 | ↓ 3.7 | 0.003 | 0.80 |
| IL-6 | 3.1 ± 0.8 | 17 | 1.1 ± 0.2 | 26 | ↑ 2.8 | 0.012 | 0.82 |
| TARC | 197 ± 62 | 12 | 77 ± 13 | 9 | ↑ 2.6 | 0.035 | 0.76 |
| IL-2 | 0.6 ± 0.1 | 16 | 0.3 ± 0.0 | 26 | ↑ 2.4 | 0.008 | 0.79 |
| IFN-γ | 1.6 ± 0.4 | 17 | 0.7 ± 0.1 | 24 | ↑ 2.4 | 0.010 | 0.70 |
| IL-10 | 2.9 ± 1.3 | 16 | 1.8 ± 0.3 | 26 | ↑ 1.6 | 0.191 | 0.61 |
| IL-12p70 | 1.1 ± 0.2 | 16 | 1.6 ± 0.3 | 26 | ↓ 1.5 | 0.079 | 0.53 |
| IL-8 | 4.2 ± 0.4 | 24 | 2.9 ± 0.2 | 26 | ↑ 1.4 | 0.002 | 0.72 |
| TNF-α | 7.3 ± 1.5 | 17 | 5.5 ± 0.4 | 26 | ↑ 1.3 | 0.131 | 0.56 |
| MCP-1 | 269 ± 33 | 12 | 219 ± 13 | 9 | ↑ 1.2 | 0.082 | 0.73 |
| MDC | 2.51 ± 0.28 (ng/ml) | 12 | 2.17 ± 0.18 (ng/ml) | 9 | ↑ 1.2 | 0.145 | 0.70 |
| MIP-1β | 67.4 ± 9.6 | 12 | 58.4 ± 5.9 | 9 | ↑ 1.2 | 0.207 | 0.60 |
| GM-CSF | 1.2 ± 0.3 | 17 | 1.4 ± 0.4 | 23 | ↓ 1.2 | 0.297 | 0.55 |
| MCP-4 | 414 ± 69 | 12 | 367 ± 67 | 9 | ↑ 1.1 | 0.306 | 0.56 |
| IP-10 | 187 ± 34 | 12 | 207 ± 38 | 9 | ↓ 1.1 | 0.346 | 0.57 |
| BDNF | 1.03 ± 0.16 (ng/ml) | 15 | 0.96 ± 0.20 (ng/ml) | 10 | ↑ 1.1 | 0.383 | 0.53 |
| Eotaxin-3 | 6.5 ± 0.7 | 12 | 6.4 ± 1.1 | 9 | ↑ 1.0 | 0.463 | 0.55 |
| Eotaxin | 538 ± 99 | 12 | 525 ± 105 | 9 | ↑ 1.0 | 0.462 | 0.56 |
| TARC/sICAM5 | $(122.8 ± 53.9) × 10^{-3}$ | 10 | $(7.2 ± 2.5) × 10^{-3}$ | 8 | ↑ 17.1 | 0.025 | 1.00 |
| IL6/sICAM5 | $(1.9 ± 1.0) × 10^{-3}$ | 13 | $(0.2 ± 0.1) × 10^{-3}$ | 16 | ↑ 9.9 | 0.050 | 0.90 |
| IL8/sICAM5 | $(3.3 ± 1.3) × 10^{-3}$ | 18 | $(0.5 ± 0.2) × 10^{-3}$ | 16 | ↑ 6.5 | 0.017 | 0.88 |

[1]average ± sem, (pg/ml unless otherwise labeled).
[2](↑) Increased in epilepsy (↓) Decreased in epilepsy.
[3]one-tailed t-test.
[4]Area under the Curve of the ROC curve.

Any document (including but not limited to any patent, patent application, publication, and website) listed herein is hereby incorporated herein by reference in its entirety. While these developments have been disclosed with reference to specific embodiments, it is apparent that other embodiments and variations of this invention are devised by others skilled in the art without departing from the true spirit and scope of the developments. The appended claims include such embodiments and variations thereof.

The invention claimed is:

1. A method for diagnosing and treating epilepsy in a patient comprising:
   (a) contacting a plasma sample obtained from said patient with an antibody targeting tumor necrosis factor alpha (TNF-α) and an antibody targeting macrophage derived chemokine (MDC) to form biomarker-antibody complexes;
   (b) measuring the concentration of the biomarker-antibody complexes in said sample;
   (c) comparing the concentration of the biomarker-antibody complexes in said sample to the concentration of the same biomarkers in a control, wherein said patient is diagnosed with epilepsy when the concentration of TNF-α and MDC is increased in said sample relative to control; and
   (d) treating said patient to ameliorate the frequency of seizure in the patient.

2. The method according to claim 1, further comprising contacting the blood sample at least one antibody targeting one or more additional biomarker(s) selected from interleukin 1β (IL-1β), interleukin 6 (IL-6), interleukin 2 (IL-2), interferon gamma (IFN-γ), interleukin 8 (IL-8), and monocyte chemotactic protein-1 (MCP-1) and measuring the concentration of the biomarker-antibody complexes in said sample.

3. The method of claim 1, wherein the concentration of biomarker-antibody complexes is measured using ELISA.

4. A method for diagnosing and treating seizures in a patient comprising:
   (a) contacting a plasma sample obtained from said patient with an antibody targeting tumor necrosis factor alpha (TNF-α) and an antibody targeting macrophage derived chemokine (MDC) to form biomarker-antibody complexes;
   (b) measuring the concentration of the biomarker-antibody complexes in said sample;
   (c) comparing the concentration of the biomarker-antibody complexes in said sample to the concentration of the same biomarkers in a control, wherein said patient is diagnosed with seizure when the concentration of TNF-α and MDC is increased in said sample relative to control; and
   (d) treating said patient with a therapy to reduce frequency of seizure.

5. The method according to claim 4, further comprising contacting the blood sample at least one antibody targeting one or more additional biomarker(s) selected from interleukin 1β (IL-1β), interleukin 6 (IL-6), interleukin 2 (IL-2), interferon gamma (IFN-γ), interleukin 8 (IL-8), and monocyte chemotactic protein-1 (MCP-1) and measuring the concentration of the biomarker-antibody complexes in said sample.

6. The method of claim 4, wherein the concentration of the biomarker-antibody complexes is measured using ELISA.

* * * * *